(12) United States Patent
Spratt

(10) Patent No.: US 10,863,901 B2
(45) Date of Patent: Dec. 15, 2020

(54) PRESCRIPTION DETERMINATION

(71) Applicants: Carl Zeiss Vision International GmbH, Aalen (DE); Ray Steven Spratt, Petaluma, CA (US)

(72) Inventor: Ray Steven Spratt, Petaluma, CA (US)

(73) Assignee: Carl Zeiss Vision International GmbH, Aalen (DE)

( * ) Notice: Subject to any disclaimer, the term of this patent is extended or adjusted under 35 U.S.C. 154(b) by 0 days.

(21) Appl. No.: 16/532,624

(22) Filed: Aug. 6, 2019

(65) Prior Publication Data

US 2019/0361267 A1    Nov. 28, 2019

Related U.S. Application Data

(63) Continuation of application No. 16/531,303, filed on Aug. 5, 2019, now Pat. No. 10,765,313, which is a
(Continued)

(51) Int. Cl.
*A61B 3/103* (2006.01)
*A61B 3/10* (2006.01)
(Continued)

(52) U.S. Cl.
CPC ............ *A61B 3/103* (2013.01); *A61B 3/0025* (2013.01); *A61B 3/107* (2013.01); *A61B 3/1015* (2013.01);
(Continued)

(58) Field of Classification Search
CPC .... G02C 7/028; G02C 2202/22; G02C 7/027; A61B 3/0025; A61B 3/1015; A61B 3/107
(Continued)

(56) References Cited

U.S. PATENT DOCUMENTS 6,241,355 B1    6/2001    Barsky
6,382,795 B1    5/2002    Lai
(Continued)

FOREIGN PATENT DOCUMENTS

CN        2770573 Y    4/2006
CN      201061523 Y    5/2008
(Continued)

OTHER PUBLICATIONS

Jayoung Nam, Larry N Thibos, and D Robert Iskander. Ocular aberrations with wavefront vergence map. Clin Exp Optom 2009; 92: 3: 194-205. DOI:10.1111/j.1444-0938.2009.00358.x (Year: 2009).*
(Continued)

*Primary Examiner* — Collin X Beatty
(74) *Attorney, Agent, or Firm* — Thrive IP®; Georg M. Hasselmann

(57) ABSTRACT

A method, a system and a computer program for determining an eyeglass prescription for an eye are disclosed. Initially, information about a measurement indicative of the refractive properties of the eye is received. Subsequently, a mathematical representation of wavefront aberrations of the eye is determined from the measurement. The mathematical representation includes a multitude of polynomials, each polynomial having an azimuthal order and a radial order. Further, the mathematical representation includes at least a first polynomial group having a common radial order, wherein the common radial order is higher than two. The eyeglass prescription is determined based on a merit function, wherein each polynomial of the first polynomial group that is used in the merit function has an azimuthal order of −2, 0, or 2, respectively.

7 Claims, 8 Drawing Sheets

Related U.S. Application Data continuation of application No. PCT/US2018/017086, filed on Feb. 6, 2018, which is a continuation of application No. PCT/US2017/016852, filed on Feb. 7, 2017.

(51) Int. Cl.
*G02C 7/02* (2006.01)
*A61B 3/00* (2006.01)
*A61B 3/107* (2006.01)

(52) U.S. Cl.
CPC ............ *G02C 7/027* (2013.01); *G02C 7/028* (2013.01); *G02C 2202/22* (2013.01)

(58) Field of Classification Search
USPC .................................................. 359/159.76
See application file for complete search history.

(56) References Cited

U.S. PATENT DOCUMENTS

| | | | |
|---|---|---|---|
| 7,857,451 | B2 | 12/2010 | Thibos et al. |
| 8,205,987 | B2 | 6/2012 | Meister et al. |
| 8,777,414 | B2 | 7/2014 | Cabeza-Guillen et al. |
| 2003/0133074 | A1* | 7/2003 | Pettit .................. A61F 9/00806 351/212 |
| 2005/0057723 | A1* | 3/2005 | Wakil .................... A61B 3/107 351/246 |
| 2005/0105047 | A1* | 5/2005 | Smitth, III ............... G02C 7/04 351/159.07 |
| 2005/0110946 | A1 | 5/2005 | Youssefi et al. |
| 2005/0213040 | A1* | 9/2005 | Gross .................. A61B 3/0025 351/243 |
| 2007/0279586 | A1* | 12/2007 | Jethmalani ............... G02C 7/02 351/159.41 |
| 2008/0100800 | A1 | 5/2008 | Guillen et al. |
| 2009/0015787 | A1 | 1/2009 | Guillen et al. |
| 2009/0079940 | A1* | 3/2009 | Dai ..................... A61B 3/0025 351/246 |
| 2010/0039614 | A1 | 2/2010 | Morris et al. |
| 2011/0149239 | A1 | 6/2011 | Neal et al. |
| 2012/0069297 | A1 | 3/2012 | Cabeza et al. |
| 2013/0179297 | A1* | 7/2013 | Yamakaji ............... G02C 7/025 705/26.5 |
| 2014/0333897 | A1 | 11/2014 | Becken et al. |

FOREIGN PATENT DOCUMENTS

| | | |
|---|---|---|
| DE | 60121123 T2 | 2/2007 |
| EP | 2063760 A2 | 6/2009 |
| EP | 2592995 A1 | 5/2013 |
| EP | 2878989 A1 | 6/2015 |
| WO | 03092485 A1 | 11/2003 |
| WO | 2005058136 A2 | 6/2005 |
| WO | 2008077006 A1 | 6/2008 |
| WO | 2008083015 A2 | 7/2008 |
| WO | 2013058725 A1 | 4/2013 |
| WO | 2014123546 A1 | 8/2014 |

OTHER PUBLICATIONS

International Search Report issued in International patent application PCT/US2017/016852, to which this application claims priority, dated Nov. 15, 2017.

Invitation under PCT article 17(3)a issued in PCT/US2018/017086, to which this application claims priority, dated Apr. 26, 2018.

International Search Report issued in International patent application PCT/US2018/017086, to which this application claims priority, dated Jul. 17, 2018.

Written opinion issued in PCT/US2018/017086, to which this application claims priority, dated Jan. 3, 2019.

International Preliminary Examination Report issued in International patent application PCT/US2018/017086, to which this application claims priority, dated May 21, 2019.

Office action by the Chinese Patent Office issued in CN 201880010729.3, which is a counterpart hereof, dated Mar. 9, 2020, and English-language translation thereof.

\* cited by examiner

PRESCRIPTION DETERMINATION

CROSS REFERENCE TO RELATED APPLICATIONS

This application is a continuation application of U.S. patent application Ser. No. 16/531,303, filed Aug. 5, 2019, which is a continuation application of international application PCT/US2018/017086, filed Feb. 6, 2018, which is a continuation of international patent application PCT/US2017/016852, filed on Feb. 7, 2017, all of which are hereby incorporated by reference in their entireties.

TECHNICAL FIELD

The current disclosure provides for a method for determining an eyeglass prescription for an eye, in particular through the use of a non-transitory computer readable medium. Further, a system for determining an eyeglass prescription for an eye and a computer program product are provided.

BACKGROUND

The ametropic human eye has refractive errors that in first approximation can be described in terms of a sphere, a cylinder, and an axis orientation. This is based on the assumption that a visual defect can be approximately corrected through a lens with simple surfaces such as torpids and spheres. This approximation may correct an error in the refraction of light rays that enter the center of the eye pupil.

While it is customary to determine the refractive errors of the human eye by relying on the subjective refraction of the patient under examination when presenting to him a plurality of optotypes through lenses of different refractive power, so-called subjective refraction or manifest refraction, the possibility of measuring the refractive errors of the eye has now been available for several years with the so-called objective refraction. Moreover, it is possible to measure the refractive power of the eye over the entire pupil. The measurable errors include for example spherical aberration, coma, trefoil error, higher orders of spherical aberration, etc. In certain implementations, the objective refraction method is based on determining the wavefront of a propagating light bundle. The functional principal of a wavefront refractor is described in document U.S. Pat. No. 6,382,795 B1, and also includes a synopsis of a plurality of different variants.

The refractive errors or imaging errors of the human eye can be mathematically described by means of so-called Zernike polynomials. The errors of the eye in regard to sphere, cylinder, and axis can be described, for example, through second-order Zernike polynomials. These errors are therefore often referred to as second-order aberrations or lower order aberrations. Further errors can be described through higher-order Zernike polynomials. Therefore, these errors are in general referred to as higher-order aberrations. The information gained from a wavefront refractor can be used in the development of improved vision aids or improved eyesight correction methods. A well-known example for an eyesight correction method is the procedure of wavefront-guided refractive surgery. In this procedure, a volume of any desired geometry is removed from the surface of the cornea in order to correct refractive errors, including those of a higher order. In general, in order to determine an eyeglass prescription for visual aids, an eye care professional determines several parameters. In the case of spectacle lenses, for example, the most relevant ones are: refractive values, usually given in form of sphere, cylinder, and axis; fitting parameters, such as pupil distance, fitting height, pantoscopic angle, and others; and near vision addition, for example, in case of progressive lenses. For contact lenses, the set of parameters usually includes at least the refractive values, similar to spectacle lenses, and corneal curvature.

A basic criterion for objective refraction algorithms was suggested to be that the objective refraction that most closely matches the subjective refraction data is considered best. This was for example suggested in document U.S. Pat. No. 7,857,451 B2. Document U.S. Pat. No. 7,857,451 B2 shows a method and system for determining the appropriate refraction prescription in the clinical optometry or ophthalmology setting. Data in the form of aberrometric input, patient history and other information, and/or other environmental data are used to optimize a real-world prescription for an individual's optic needs through the use of an equivalent quadratic fitting calculation or a simulated through-focus experiment. A corresponding disclosure is made in document WO 2013/058725 A1 of the same patent family.

Wavefront aberration data is used to obtain the objective estimates of optimal second order corrections for wearers. These prescriptions obtained by objective refraction can sometimes vary significantly from the same wearer's prescription obtained via subjective refraction. This may be disadvantageous if the previous or new subjective prescription is judged superior.

Document US 2005/0057723 A1 shows method of measuring eye refraction to achieve desired quality according to a selected vision characteristics comprising the steps of selecting a characteristic of vision to correlate to the desired quality of vision from a group of vision characteristics comprising acuity, Strehl ratio, contrast sensitivity, night vision, day vision, and depth of focus, dynamic refraction over a period of time during focus accommodation, and dynamic refraction over a period of time during pupil constriction and dilation; using wavefront aberration measurements to objectively measure the state of the eye refraction that defines the desired vision characteristic; and expressing the measured state of refraction with a mathematical function to enable correction of the pre-selected vision characteristic to achieve the desired quality of vision. The mathematical function of expression may be a Zernike polynomial having both second order and higher order terms or a function determined by spline mathematical calculations. The pre-selected desired vision characteristics may be determined using ray tracing technology.

There remains a need in the art to determine an eyeglass prescription for an eye that only has a small optical difference to the prescription obtained via subjective refraction.

SUMMARY

It is an aspect of the disclosure to provide a computer-implemented method for determining an eyeglass prescription for an eye, in particular through the use of a non-transitory computer-readable medium, the method comprising the steps of:

receiving information about a measurement indicative of the refractive properties of the eye;

determining a mathematical representation of wavefront aberrations of the eye from the measurement, wherein the mathematical representation comprises a multitude of polynomials, each polynomial having an azimuthal order and a radial order, wherein the mathematical representation comprises at least a first polynomial group having a common radial order, wherein the common radial order is higher than two;

determining the eyeglass prescription based on a merit function, and wherein each polynomial of the first polynomial group that is used in the merit function has an azimuthal order of −2, 0, or 2, in particular wherein the merit function comprises at least one polynomial of the mathematical representation.

Instead of "azimuthal" order, the terms of "angular order "or" meridional order" could also be used. Current solutions use a reasonably large set of Zernike polynomials to represent the wavefront aberrations of the measured eyes. For example, all terms of a Zernike description of wavefront aberrations of the eye for radial orders 2 through 7 could be used. The assumption is that this representation closely matches the actual wearer's aberrations and, therefore, using them in determination whatever metric is used for optical performance should yield the best results. However, as laid out in further detail below, it was found that at least many, if not almost all of these Zernike terms represent "noise" that reduce the accuracy of the determination in a sense that it moved the prescription determined via objective refraction means away from the prescription obtained via subjective refraction. The prescription found via subjective refraction was defined as the target and considered to be the best prescription for the wearer.

Hence, it is suggested to determine the eyeglass prescription based on a merit function wherein each polynomial of the first polynomial group that is used in the merit function has an azimuthal order of −2, 0, or 2. In particular, all three polynomials, as far as present, within the first polynomial group of azimuthal orders of −2, 0, and 2 can be used. Of course, further to the first polynomial group having a common radial order there may be further polynomial groups, i.e. a second, a third, fourth, fifth etc. polynomial group in which the polynomials have a common radial order that is different from that of the first polynomial group. In general, the current disclosure proposes two general exemplary embodiments to achieve that each polynomial within the merit function used comprises only angular orders of −2, 0, or 2. A first general exemplary embodiment determines the mathematical representation of the wavefront aberrations of the eye only with polynomials of angular orders −2, 0, and/or 2. By developing the mathematical representation of the wearer's eye already based on this boundary condition, it will be ensured that the merit function only comprises such terms. In a second general exemplary embodiment, the description of the wavefront aberrations of the wearer's eye are expressed differently and comprise polynomials not having an angular order −2, 0, or 2. For example, the wavefront aberrations are expressed with Zernike polynomials and the corresponding coefficients as well known to the person skilled in the art. However, only a reduced subset of polynomials from this wavefront description is then actually used in the determination of the eyeglass prescription, in particular in the merit function. The merit function comprises at least one polynomial of the mathematical representation, in particular the merit function may comprise at least three polynomials of the mathematical representation, In an exemplary embodiment, only nine Zernike polynomials through seventh radial order are kept, namely those with angular orders −2, 0, and 2. In fact, only those Zernike polynomials with the same angular dependence as the eventual corrections, namely sphere, cylinder, and axis, for example, are used.

According to a second aspect of the current disclosure, there is provided a computer implemented method for determining an eyeglass prescription for an eye, in particular through the use of a non-transitory computer readable medium, the method comprising the steps of:

receiving information about a measurement indicative of the refractive properties of the eye;

determining a mathematical representation of wavefront aberrations of the eye from the measurement, wherein the mathematical representation comprises a multitude of terms, wherein each term comprises a function dependent on the pupil radius, and wherein each term of the mathematical representation is either independent of an azimuthal angle or has a dependency on an azimuthal angle expressed by at least one of $\sin(2\Theta)$ and $\cos(2\Theta)$ with $\Theta$ being the azimuthal angle; and determining the eyeglass prescription based on a merit function, and wherein the merit function comprises at least one term of the mathematical representation.

For example, the function dependent on the pupil radius of each term may be a polynomial, wherein each polynomial has a radial order, and wherein the highest radial order is higher than two.

As another example, the function dependent on the pupil radius of each term may be a Fourier series. As an even further example, the function dependent on the pupil radius of each term may be a spline function.

In particular, the merit function may comprise all terms of the mathematical representation.

Further, there is provided according to a third aspect of the current disclosure a computer-implemented method for determining an eyeglass prescription for an eye, in particular through the use of a non-transitory computer readable medium, the method comprising the steps of:

receiving information about a measurement indicative of the refractive properties of the eye;

determining a mathematical representation of wavefront aberrations of the eye from the measurement, wherein the mathematical representation comprises a multitude of polynomials, each polynomial having an azimuthal order and a radial order, wherein the mathematical representation comprises a polynomial group having a common radial order, wherein the common radial order is even and higher than two;

determining the eyeglass prescription based on a merit function, and wherein the merit function only comprises the polynomials of the polynomial group having an azimuthal order of −2, 0 and 2, respectively, in particular wherein the merit function comprises at least one polynomial of the mathematical representation.

The methods according to the first to third and ninth aspects are computer-implemented methods for determining an eyeglass prescription for an eye. The measurement information indicative of the refractive properties of the eye is received by the computer or processing unit. In other words, the measurement information indicative of the refractive properties of the eye is provided. Further disclosed are methods for determining an eyeglass prescription for an eye wherein a step of measuring or conducting a measurement indicative of the refractive properties of the eye is included. Hence, an actual measurement is conducted. For example, such a method may include a step of conducting a measurement indicative of the refractive properties of the eye prior to or instead of receiving information about a measurement indicative of the refractive properties of the eye and may further include all further steps of a respective one of the methods according to the first to third aspects.

Even further, according to a fourth aspect of the current disclosure, there is provided a method for manufacturing a spectacle lens, the method comprising the steps of determining an eyeglass prescription according to a first aspect of the disclosure or one of its exemplary embodiments, the second aspect of the current disclosure or one of its exemplary embodiments or the third aspect of the current disclosure or one of its exemplary embodiments, and manufacturing the spectacle lens according to the eyeglass prescription.

Further, according to a fifth aspect of the current disclosure, there is provided a system for determining an eyeglass prescription for an eye, comprising a processing unit configured to receive information about a measurement indicative of the refractive properties of the eye, to determine a mathematical representation of the refractive properties of the eye, wherein the mathematical representation comprises a multitude of polynomials, each polynomial having an azimuthal order and a radial order, wherein the mathematical representation comprises at least a first polynomial group having a common radial order, wherein the common radial order is higher than two, and to determine the eyeglass prescription based on a merit function, and wherein each polynomial of the first polynomial group and used in the merit function has an azimuthal order of −2, 0, or 2, Even further, according to a sixth aspect of the disclosure there is provided a, particular non transitory, computer program product comprising program code means for carrying out the steps of a method according to the first aspect of the disclosure or one of its exemplary embodiments, or the second aspect of the disclosure or one of its exemplary embodiments or the third aspect of the disclosure or one of its exemplary embodiments, or of the ninth aspect of the disclosure or one of its exemplary embodiments, in particular when the computer program product is run on a computer or processing unit.

Further, according to a seventh aspect of the current disclosure, there is provided a system for determining an eyeglass prescription for an eye, comprising a processing unit configured to receive information about a measurement indicative of the refractive properties of the eye, to determine a mathematical representation of wavefront aberrations of the eye from the measurement, wherein the mathematical representation comprises a multitude of terms, wherein each term comprises a function dependent on the pupil radius, and wherein each term of the mathematical representation is either independent of an azimuthal angle or has a dependency on an azimuthal angle expressed by at least one of $\sin(2\Theta)$ and $\cos(2\Theta)$ with $\Theta$ being the azimuthal angle, and to determine the eyeglass prescription based on a merit function, wherein the merit function comprises at least one term of the mathematical representation.

Further, according to an eighth aspect of the current disclosure, there is provided a system for determining an eyeglass prescription for an eye, comprising a processing unit configured to receive information about a measurement indicative of the refractive properties of the eye, to determine a mathematical representation of wavefront aberrations of the eye from the measurement, wherein the mathematical representation comprises a multitude of polynomials, each polynomial having an azimuthal order and a radial order, wherein the mathematical representation comprises a polynomial group having a common radial order, wherein the common radial order is even and higher than two, and to determine the eyeglass prescription based on a merit function, wherein the merit function comprises at least one polynomial of the mathematical representation, and wherein the merit function only comprises the polynomials of the polynomial group having an azimuthal order of −2, 0, and 2, respectively, Further, according to a ninth aspect of the current disclosure, there is provided a computer-implemented method for determining an eyeglass prescription for an eye, the method comprising the steps of:

receiving information about a measurement indicative of the refractive properties of the eye; and determining a mathematical representation of wavefront aberrations of the eye from the measurement, wherein the mathematical representation comprises a multitude of linearly independent functions, each function having an azimuthal order and a radial order, wherein the mathematical representation comprises at least a first group of functions having a common radial order, wherein the common radial order is higher than two; and determining the eyeglass prescription based on a merit function, wherein the merit function comprises at least one function of the mathematical representation, and wherein each function of the first group of functions that is used in the merit function has an azimuthal order of −2, 0, or 2, wherein the merit function has a non-linear dependency on coefficients of the multitude of linearly independent functions.

A common example for a multitude of linearly independent functions that could be used according to the disclosure are Zernike polynomials. Zernike polynomials are a common measure to report optical aberrations of the eye, cf. ANSI Z80.28-2010. Other linearly independent functions or that might be used instead of Zernike polynomials may be two dimensions visions of a Taylor series, a Fourier-Bessel series, or a Fourier series. A Zernike polynomial series and a Fourier-Bessel series are also orthogonal over a circular pupil. All orthogonal series are linearly independent. Hence, in particular, the multitude of linearly independent functions is orthogonal.

Further, according to a tenth aspect of the current disclosure, there is provided a system for determining an eyeglass prescription for an eye, comprising a processing unit configured to receive information about a measurement indicative of the refractive properties of the eye, to determine a mathematical representation of the refractive properties of the eye, wherein the mathematical representation comprises a multitude of polynomials, each polynomial having an azimuthal order and a radial order, wherein the mathematical representation comprises at least a first polynomial group having a common radial order, wherein the common radial order is higher than two, and to determine the eyeglass prescription based on a merit function, wherein the merit function comprises at least one polynomial of the mathematical representation, and wherein each polynomial of the first polynomial group and used in the merit function has an azimuthal order of −2, 0, or 2, the merit function has a non-linear dependency on coefficients of the multitude of linearly independent functions.

In general, throughout the current application, reference is made to Zernike polynomials. Concerning the usage of Zernike polynomials in ophthalmology, and in the context of the current application, the definitions made in the standard ANSI Z80.28-2010"Ophthalmics-Methods of Reporting Optical Aberrations of Eyes" shall apply.

Hence, the object initially outset is fully achieved.

The following exemplary embodiments apply to each of the methods according to the first to third and ninth aspects for determining an eyeglass prescription for an eye, as well as to the method for manufacturing a spectacle lens and the system for determining an eyeglass prescription for an eye.

According to an exemplary embodiment, from polynomials of the mathematical representation having a radial order below 3, the merit function only comprises or is only based on polynomials having the second radial order.

By this, the mathematical representation is further reduced. From low order polynomials, namely polynomials having a radial order below 3, only second radial order polynomials are included in the determination of the merit function.

According to a further exemplary embodiment, the determination of an eyeglass prescription may comprise the further step of establishing an optimization space corresponding to a plurality of possible eyeglass prescriptions for the eye, and wherein the eyeglass prescription is determined by optimizing a value of the merit function, wherein the value of the merit function corresponds to a visual function of the eye when corrected using one of the plurality of possible eyeglass prescriptions within the optimization space.

By this, the eyeglass prescription is determined via an optimization procedure finding a prescription that provides for an optimized value of the merit function.

According to a further exemplary embodiment, the merit function has a non-linear dependency on coefficients of the multitude of polynomials.

The multitude of polynomials has a multitude of respective coefficients. More complex merit functions can be developed used by allowing non-linear dependency of the merit function on the polynomials, in order to find a better prescription.

Other linearly independent functions that might be used instead of Zernike polynomials may be two dimensions versions of a Taylor series, a Fourier-Bessel series, or a Fourier series. A Zernike polynomial series and a Fourier-Bessel series are also orthogonal over a circular pupil. An orthogonal series are linearly independent.

Hence, in a further exemplary embodiment, the multitude of linearly independent functions is orthogonal.

According to a further exemplary embodiment, the common radial order of the first polynomial group is even, wherein the merit function only comprises three polynomials having an azimuthal order of −2, 0, and 2, respectively, of the first polynomial group.

By this, the first polynomial group is reduced to comprise only three polynomials, namely those having azimuthal or angular order of −2, 0, and 2. All further polynomials are not used in the determination of the prescription.

In a further exemplary embodiment, only a reduced number of polynomials having the common radial order is used in the merit function compared to a number of polynomials within the first polynomial group of the mathematical representation, and wherein the reduced polynomial group used in the merit function only comprises polynomials having an azimuthal order of −2, 0, or 2.

Accordingly, the mathematical representation is developed based on an approach involving more polynomials within the first polynomial group than subsequently used when determining the prescription. However, it has been found that using only those polynomials within the first polynomial group having the azimuthal or angular order of −2, 0, and/or 2 will provide for a determined objective eyeglass prescription closer to that determined via subjective refraction.

In general, the first polynomial group having a common radial order may have third radial order, fourth radial order, fifth radial order, sixth radial order, or seventh radial order.

According to a further exemplary embodiment, the first polynomial group and the mathematical representation comprises polynomials each having a radial order different from −2, 0, and 2, and wherein no polynomial of the first polynomial group is used in the merit function.

Hence, since the current disclosure requires each polynomial within the first polynomial group and being used within the merit function to have an azimuthal or angular order of −2, 0, or 2, it may happen that, depending on the mathematical representation, actually no polynomial of the first polynomial group is used within the merit function. One example may be an expression of the wavefront aberrations via Zernike polynomials. For example, Zernike polynomials of the third radial order do not comprise a polynomial having an azimuthal order of −2, 0, or 2. Hence, no Zernike polynomials of the third radial order would be used within the merit function in case the third radial order is the common radial order of the first polynomial group.

According to a further exemplary embodiment, the mathematical representation is determined using Zernike polynomials.

Zernike polynomials are a common measure to report optical aberrations of the eye, cf. ANSI Z80.28-2010.

According to a further exemplary embodiment, the mathematical representation includes Zernike polynomials up to and including seventh radial order, wherein the merit function is based only on Zernike polynomials of the second radial order and Zernike polynomials having a radial order higher than 2.

The mathematical representation includes 33 Zernike polynomials in total from second through seventh radial order. A subset of these may then be chosen for the determination of the eyeglass prescription.

According to a further exemplary embodiment, the common radial order of the first polynomial group is the third order, the fourth order, the fifth order, the sixth order, or the seventh order.

Hence, the polynomials of any order may form the first polynomial group to be reduced according to the current disclosure. In particular, further to the first polynomial group, a mathematical representation may comprise further polynomial groups, in particular a second polynomial group, a third polynomial group, a fourth polynomial group, and/or a fifth polynomial group. Each of these polynomial groups may have a different common radial order. Each of these common radial orders may be one of the third to seventh radial orders.

According to a further exemplary embodiment, in case the common radial order of the first polynomial group is even, the merit function only comprises the polynomials of azimuthal orders of −2, 0, and 2, respectively, and, in case the common radial order of the first polynomial group is odd, the merit function comprises no polynomial of the first polynomial group.

Hence, for odd Zernike polynomial orders, no polynomials are used for the determination of the merit function. In case the common radial order is even, for example fourth or sixth radial order, the polynomials of azimuthal orders −2, 0, and 2 are used. In an extreme case, for the mathematical representation comprising Zernike polynomials of second through seventh order, only nine Zernike polynomials will be used for determination of the merit function, namely both having azimuthal orders of −2, 0, and 2 within the second, fourth, and sixth radial orders.

According to a further exemplary embodiment, the mathematical representation comprises at least a second polynomial group having a common radial order and different from the first polynomial group, wherein the common radial order of the second polynomial group is higher than two, and wherein, in case the common radial order of the second polynomial group is even, the merit function only comprises the polynomials of azimuthal orders of −2, 0, and 2, respectively, and, in case the common radial order of the second polynomial group is odd, the merit function comprises no polynomial of the second polynomial group.

As already outlined above, the reduction according to the current disclosure can be applied to a multitude of polynomial groups of the Zernike expression. Hence, there may be at least a second polynomial group further to the first polynomial group. In particular, each higher radial order, namely each radial order above 2 may form a polynomial group.

In the further exemplary embodiment, the merit function only comprises Zernike polynomials having an azimuthal order of −2, 0, and 2, respectively.

In order words, the merit function is only based on Zernike polynomials having an azimuthal or angular or meridional order of −2, 0, and 2. For the example of the mathematical representation comprising Zernike polynomials of second through seventh radial orders, this would result in nine Zernike polynomials as outlined above.

In a further exemplary embodiment, the mathematical representation comprises at least a second polynomial group having a common radial order and different from the first polynomial group, wherein the common radial order of the second polynomial group is higher than two, and wherein, of each polynomial group having an even radial order, the merit comprises all Zernike polynomials, and wherein, of each polynomial group having an odd order, the merit function comprises no polynomial.

In other words, according to this exemplary embodiment, the Zernike polynomials having an odd radial order above 2 are not used and deleted. However, all Zernike polynomials having an even radial order above 2 are kept and used in the merit function.

According to a further exemplary embodiment, the mathematical representation is determined to comprise only polynomials having azimuthal order of −2, 0, or 2.

Hence, in this case, the mathematical representation is initially determined such that only azimuthal orders of −2, 0, or 2 are used. Via this mathematical approach for the mathematical representation of the wavefront aberrations of the eye, it can be ensured that the resulting eyeglass prescription is closer to the prescription determined via subjective refraction techniques.

In a further exemplary embodiment, the mathematical representation is determined in the form of $$W = f_{-2}(r)\cos(2\cdot\Theta) + f_0(r) + f_2(r)\sin(2\cdot\Theta),$$

wherein $f_{-2}(r)$, $f_0(r)$, and $f_2(r)$ are functions of the radius of a pupil of the eye, and wherein W is the wavefront aberration of the eye. In this equation, $\Theta$ is the azimuthal angle, or the angle of the polar coordinate system.

In this approach, a mathematical representation resulting in an eyeglass prescription determined via objective refraction closer to the subjective refraction prescription can be achieved. The functions of the radius of the pupil of the eye can be determined in any radial order above second order, in particular a third, fourth, fifth, sixth, or seventh order.

In a further exemplary embodiment, in particular for the system, a measurement device for measuring the refractive properties of the eye, wherein the measurement device is located at a first site, wherein the processing unit is located at a second site, and wherein the first site and the second site are connected via a data network.

By this, the measurement and the determination of the eyeglass prescription can be conducted at different sites. By this, any ophthalmologist can be provided with the advantage of the prescription determination even if he is located remote from corresponding determination facilities.

In a further exemplary embodiment, optimizing the value of the merit function comprises iteratively determining a corrected wavefront indicative of the refractive properties of the eye and the corresponding possible eyeglass prescription. By this, based on each possible eyeglass prescription, the corrected wavefront is determined. Based on the corrected wavefront, a corresponding value of the merit function is calculated. The value of the merit function depends on which visual function of the eye is used to build the merit function and to provide the corresponding values of the merit function.

Different kinds of merit functions and optimization metrics to provide results of objective refraction techniques have been contemplated and are well known to a person skilled in the art. Examples are given for example in document U.S. Pat. No. 7,857,451 B2 "System and method for optimizing clinical optic prescriptions," document US 2012/0069297 A1 "Eyeglass prescription method," US 2005/0110946 A1 "Objective manifest refraction," WO 03/092485 A1 "Sharpness metric for vision quality," US 2008/0100800 A1 "Eyeglass prescription method," US 2009/0015787 A1 "Apparatus and method for determining an eyeglass prescription for a vision defect of an eye," and document U.S. Pat. No. 8,205,987 B2 "Method for optimizing a spectacle lens for the wavefront aberrations of an eye."

The features mentioned above and the features to follow cannot only be used in the combinations provided but also in different combinations or alone without departing from the scope of the current disclosure.

BRIEF DESCRIPTION OF THE DRAWINGS

The disclosure will now be described with reference to the drawings wherein.

DESCRIPTION OF EXEMPLARY EMBODIMENTS

Figure 1:
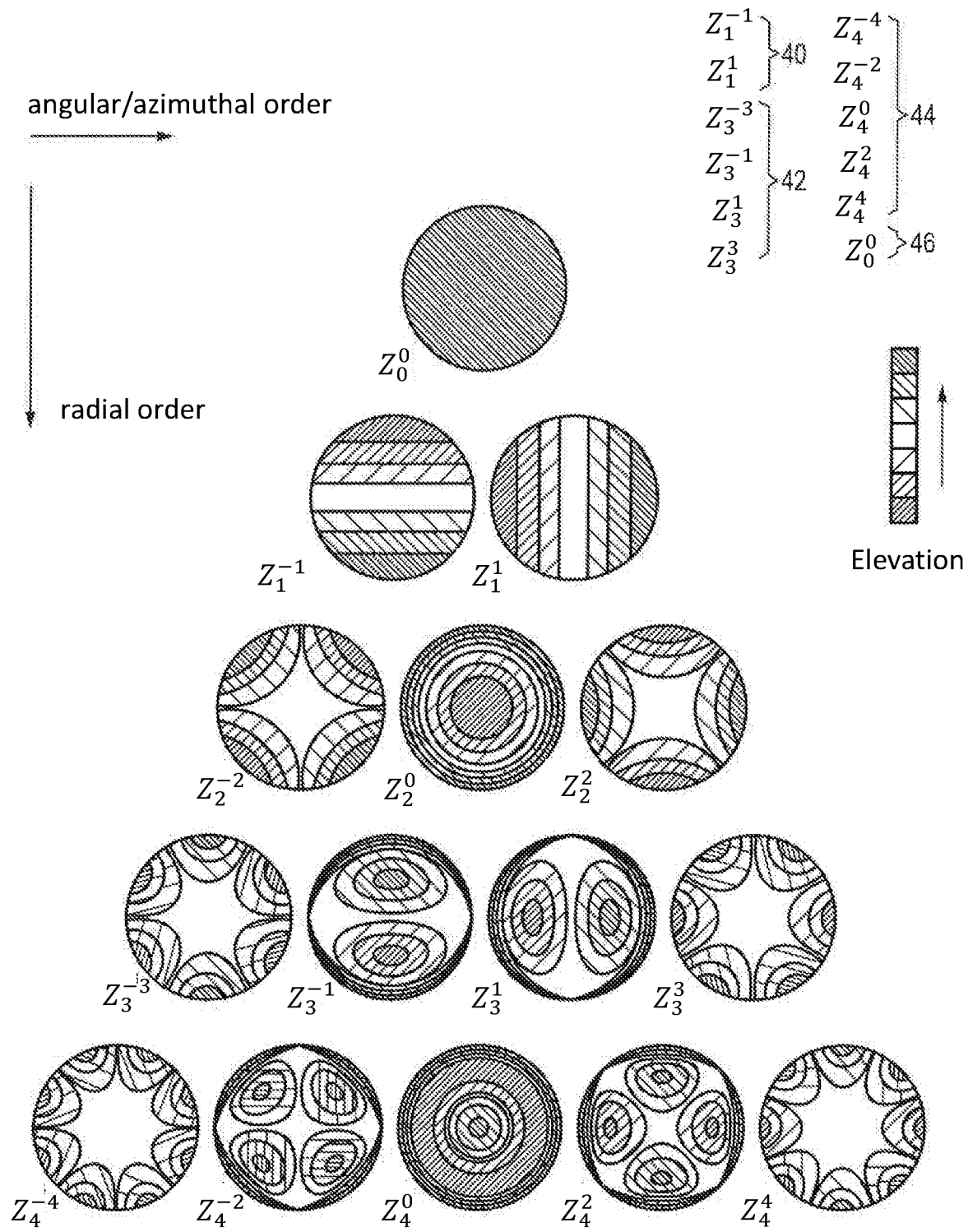
FIG. 1 shows an example set of Zernike polynomials for explaining general items of the disclosure.

FIG. 1 shows the generally known Zernike polynomials for describing optical aberrations over the pupil of an eye.

The Zernike polynomials from order zero up to fourth radial order are shown as an example. From top to bottom, the radial order increases from order zero to fourth radial order. From left to right, the angular order increases. The angular order is also called azimuthal order or meridional order. The polynomials are designated in the form of $Z_n^m$, wherein n is the radial order and m is the angular order. Concerning the generally applicable conventions regarding Zernike polynomials, reference is made to standard ANSIZ80.28-2010.

In the current application, reference is made to at least a first polynomial group having a common radial order. As a mathematical representation of the optical aberrations of an eye, a set of polynomials is used. Typically, the three polynomials of the second radial order are used plus further higher order aberrations, i.e. aberrations above the second radial order. FIG. 1 shows higher order aberrations of third and fourth radial order, further higher order aberrations might be included, for example up to and including seventh radial order. No matter what mathematical approach is used for the mathematical representation of the aberrations of the eye, all polynomials sharing a common radial order shall form a polynomial group. Such polynomial group may then comprise one or more polynomials. Corresponding groups of polynomials are hence designated by reference numerals 40, 42, 44, and 46, According to the current disclosure, the polynomial groups, in particular the first polynomial group, have a radial order above 2. Hence, for example the polynomial group 42 of third radial order or the polynomial group 44 of fourth radial order may form the first polynomial group. Of course, a mathematical representation could, for example, comprise Zernike polynomials from radial orders 2, 3, and 4. Then, the mathematical representation would have two polynomial groups, a first group of, for example, third radial order and a second group of fourth radial order. Of course, the mathematical representation can be further extended, for example, up to and including seventh radial order. Then a mathematical representation would include in total five polynomial groups, i.e. first to fifth polynomial groups, which have third, fourth, fifth, sixth, and seventh radial order, respectively.

In general, and in advance, it has been found that in case Zernike polynomials are used, an eyeglass prescription can be determined closer to an eyeglass prescription determined via subjective refraction in case only polynomials having an angular order of 2, 0, and/or −2 are used. For example in case of polynomial group 42 having third radial order, this would mean that no polynomial of third radial order would be used in the calculation of the merit function for determining the eyeglass prescription. In case of even orders, for example polynomial group 44 having fourth radial order, this would mean that only a reduced number of polynomials would be used, namely those having an angular order of −2, 0, and 2. Two polynomials having an angular order of −4 and 4 would not be used.

Figure 3:
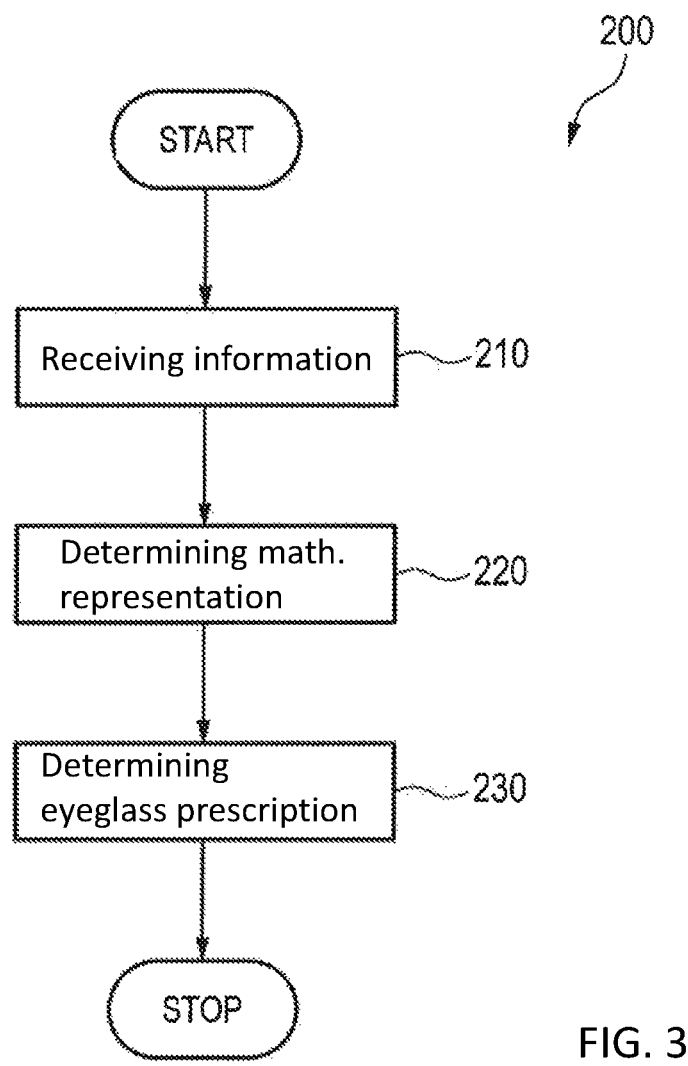
FIG. 3 shows a further exemplary embodiment of a method for determining an eyeglass prescription for an eye.
Figure 4:
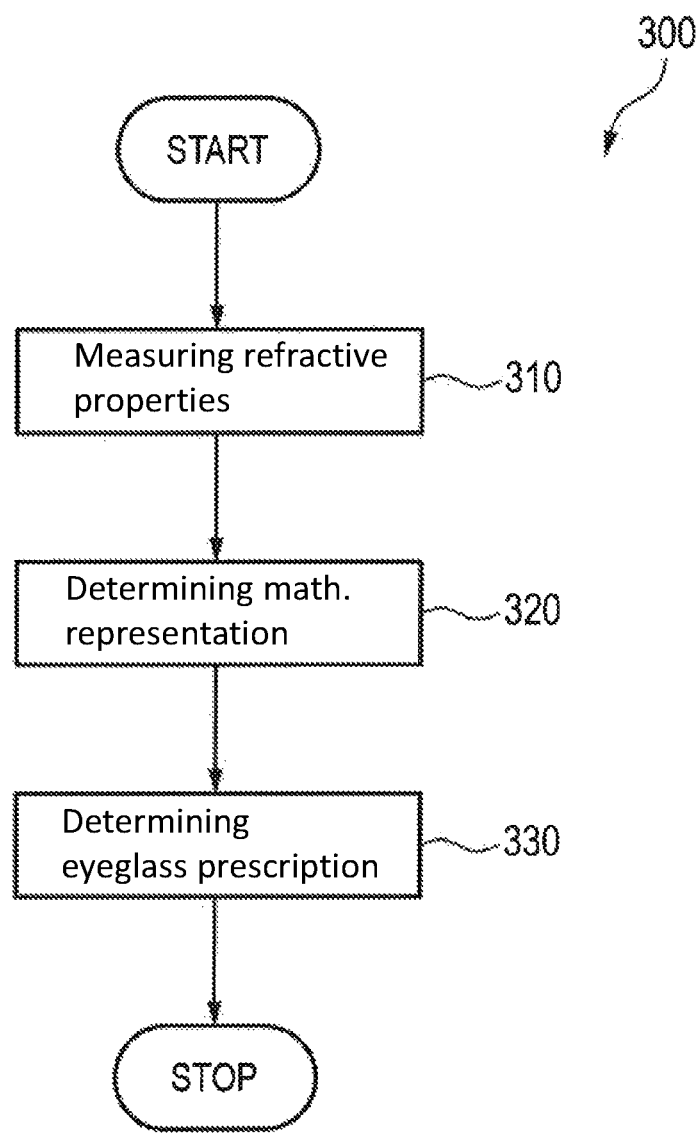
FIG. 4 shows a further exemplary embodiment of a method for determining an eyeglass prescription for an eye.

In the following, a general exemplary embodiment of the current disclosure will be explained with reference to FIG. 2. Then, two particular exemplary embodiments will be explained with reference to FIGS. 3 and 4. With reference to FIG. 3, an exemplary embodiment is disclosed in which the mathematical representation is already developed in a way that only polynomials having an angular order of −2, 0, and/or 2 are used. With reference to FIG. 4, an exemplary embodiment is disclosed that makes use of Zernike polynomials, as outlined with reference to FIG. 1, and in which only a reduced set of polynomials is used for the merit function and the determination of the eyeglass prescription that does not apply the full set of Zernike polynomials in each radial order but focuses on those polynomials having an angular order of −2, 0, and 2.

Figure 2:
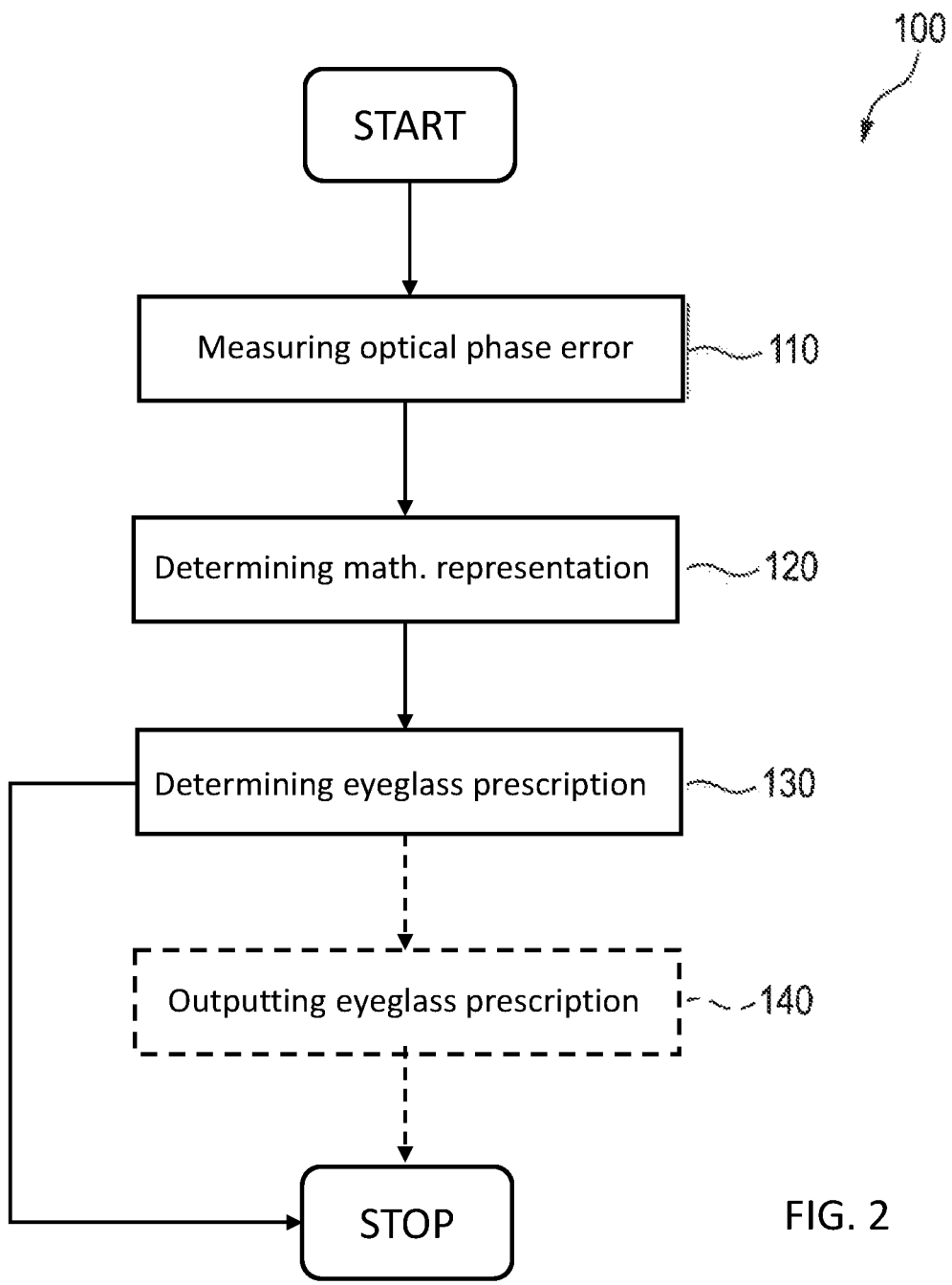
FIG. 2 shows an exemplary embodiment of a method for determining an eyeglass prescription for an eye.

Referring to FIG. 2, an exemplary embodiment of a method 100 generally includes a number of steps, as illustrated by the flow chart. In a first step, 110, the optical phase error of a patient's eye may be measured using an objective method. Typically, this involves measuring a wavefront reflected from the eye using an appropriate sensor. Examples of sensors include various wavefront aberrometers, such as Hartmann-Shack wavefront sensors, Tscherning aberrometers, Talbot aberrometers, and double-pass aberrometers.

The functional principal of a wavefront aberrometer is described in DE 60121123 T2, which also includes a synopsis of a number of different variants. However, in step 110, such measurement information or information about such a measurement indicative of the refractive properties of the eye may be provided or received.

In step 120, a mathematical representation of the measured aberrations of the eye is determined. This may be done based on a customized mathematical approach or via well-established descriptions, e.g., a set of Zernike polynomials.

The mathematical representation is used as an input for a processing unit, typically, including an electronic processor (e.g., a computer). Then, in a further step, step 130, the eyeglass prescription is determined by use of a merit function and based on the mathematical representation previously determined.

The processing unit establishes a multi-dimensional optimization space, for which the processing unit calculates a merit function corresponding to, for example, the visual acuity of the eye. The dimensions of the optimization space typically correspond to the sphero-cylindrical corrections characterizing an eyeglass prescription (e.g., sphere, cylinder, and axis). The ranges for each of the dimensions of the optimization space can be set by the professional, or preset by the processing unit. For example, the optimization space can have a certain range for each dimension, or the default can be over-ridden by the eye care professional based on the professional's experience with the patient. The values for the sphero-cylindrical corrections within each range can be established as desired. For example, each dimension can include a preset number of values (e.g., 10 or more, 100 or more), so that the incremental change between the values is determined by the range. Alternatively, or additionally, the incremental change between the values can be preset, in which case the number of values for each dimension is determined by setting the range. In some exemplary embodiments, the values can correspond to stock lens values within the range in each dimension.

As an example, an optimization space can be established based on the patient's pre-existing prescription, where the ranges for sphere and cylinder are set from −5 diopters to +5 diopters about the sphere and cylinder values of the pre-existing prescription. The values can be incremented, by example, by 0.25 diopters within each range.

Typically, the result is an optimization space that is composed of a finite number of "sphere, cylinder, axis" or "mean power ('M'), $J_0$, $J_{45}$" coordinates for which a merit function can be evaluated.

In some exemplary embodiments, the optimization space is composed of a single space. For example, each point in the optimization space can be a three component vector, e.g., having components corresponding to sphere, cylinder and axis or alternatively the Jackson cylinder components (M, $J_0$, $J_{45}$). In certain exemplary embodiments, the optimization space is divided into multiple optimization subspaces, such as two optimization subspaces. For example, each point in the first subspace can be a value for the sphere correction or defocus, and the components of a point in the second subspace can be values for cylinder and axis or the Jackson cylinder components ($J_0$, $J_{45}$). In a further step, in either case, a surface representing the wavefront of the optical correction for each co-ordinate in the optimization space or subspace is created and subtracted from the original wavefront, which yields a series of corrected wavefronts.

Then in a further step, for each of those wavefronts a merit function is calculated, which correlates with either visual acuity, contrast sensitivity or with another measure of visual performance, or correlates with a combination of those measures of visual performance.

In general, when the optimization space is divided into more than one subspace, the correction for the first subspace (e.g., sphere) should be determined first, and then subtracted from the measured wavefront before determining the correction for the second subspace (e.g., cylinder and axis).

To calculate the data, for each point in the optimization space, a corresponding corrected wavefront is calculated. The corrected wavefront is the measured wavefront corrected by the corresponding spherical correction value.

Then, a merit function value for each of the resulting corrected wave-fronts is calculated. In general, merit function values can be calculated in a variety of ways. In certain example exemplary embodiments, the merit function may be calculated according to the methods disclosed in document US 2009/0015787 A1.

For example, in some exemplary embodiments, at least two submetrics can be determined for one of the parameter sets in different stages of the propagation of light through the optical system represented by the eye and an optic corresponding to the eyeglass prescription. In other words, the light passes through the optical system represented by the eye and the optic. One now considers the deviation of the light ray compared to the ideal case, as expressed through a quality metric or submetric, when the light ray has traversed or propagated through the system represented by the eye and the correction by different travel distances. A propagation in the reverse direction, directed from the system represented by the eye and the optic towards the Object, is likewise conceivable. The propagation being considered here is not tied to a fixed direction through the system represented by the eye and the correction, but can be carried out for any desired number of directions, e.g., in general directions of the line of sight.

These submetrics can include, for example, ray quality metrics such as for example metrics that measure the Strehl ratio or the energy of the point-image washout function enclosed within the Airy disc.

An overall metric which reflects in particular the quality of the caustic or caustic metric can be determined from a weighted sum of the previously determined submetrics. In some exemplary embodiments, all submetrics are given equal weight in the determination of the overall metric or caustic metric. In certain exemplary embodiments, a submetric of a typical propagation stage is weighted more heavily than the submetrics in the propagation stages before and/or behind this typical propagation stage. If one uses for example submetrics that take the image quality in different planes into account, then the submetric for the image on the retina (which corresponds to the submetric in the typical propagation stage) would typically be given more weight than the submetric for an image before or behind the retina of the eye. The weight ratio could be for example 60/40. Detailed explanation of such an example of possible metrics is given in document US 2010/0039614 A1.

The result of this procedure leads to an optimization of the visual function for a certain solution within the optimization's base. This is the eyeglass prescription finally found to be the optimal eyeglass prescription for the wearer to correct for the wearer's eyes aberrations.

In a further optional step 140, the eyeglass prescription may be output, for example to an ophthalmologist, for example on a display device or the printer or else. Alternatively, the determined eyeglass prescription can also be forwarded to manufacturing facilities or else as will further explained with reference to this system and FIGS. 8 and 9.

FIG. 3 shows a further exemplary embodiment of a method according to the current disclosure generally designated by reference numeral 200. The method is for determining an eyeglass prescription for an eye.

In a first step, a measurement indicative of the refractive properties of the eye is obtained. It may either be measured via an aberrometer, for example, or it may be obtained as a complete data set. Hence, the measurement may be actually conducted or corresponding measurement information or information about such a measurement indicative of the refractive properties of the eye may be received. Based on the measurement, a mathematical representation of wavefront aberrations of the eye is determined. According to this exemplary embodiment, the mathematical representation comprises a multitude of terms, wherein each term comprises a function dependent on the pupil radius, and wherein each term of the mathematical representation is either independent of an azimuthal angle or has a dependency on an azimuthal angle expressed by at least one of $\sin(2\Theta)$ and $\cos(2\Theta)$ with $\Theta$ being the azimuthal angle. By this, the mathematical representation is developed via a mathematical approach that only allows for azimuthal dependencies of double frequency, i.e. comparable to an azimuthal order of −2 or 2 in case of polynomials, or allows a term to be independent of the azimuthal angle, comparable to an azimuthal order of 0 in case of polynomials.

In the further step 230 the eyeglass prescription is determined based on a merit function and the mathematical representation determined in step 220.

In particular, in step 220, the mathematical representation can be determined based on the following description:

$$W = f_{-2}(r)\cos(2\cdot\Theta) + f_0(r) + f_2(r)\sin(2\cdot\Theta),$$

wherein $f_{-2}(r)$, $f_0(r)$, and $f_2(r)$ are functions of the radius of the pupil of the eye, and wherein $W$ is the wavefront aberration of the eye.

In FIG. 4, a further exemplary embodiment of a method according to the current disclosure is shown.

The method is for determining an eyeglass prescription of an eye. In a first step 310, a measurement indicative of the refractive properties of the eye is obtained. The measurement may be received as a data set or actually conducted. Again, this may be done via an aberrometer or other objective wavefront refraction as for example outlined together with FIG. 1 for step 110.

Then, in step 320, the mathematical representation of wavefront aberrations of the eye from the measurement is determined, wherein the mathematical representation comprises a multitude of polynomials, each polynomial having an azimuthal order and a radial order. The mathematical representation comprises a polynomial group having a common radial order, wherein the common radial order is even and higher than 2.

Therefore, in this exemplary embodiment, the mathematical representation comprises higher order polynomials of an even order, for example fourth order polynomials or sixth order polynomials, for example according to the Zernike polynomial series.

Then, in step 330, the eyeglass prescription is determined based on a merit function. However, the merit function only comprises or is only based on polynomials. The polynomials of the polynomial group having an azimuthal order of −2, 0, and 2, respectively.

Hence, this exemplary embodiment, a mathematical representation is developed that comprises more polynomials than are actually used in the further determination of the eyeglass prescription. In particular, only those polynomials having an azimuthal order of −2, 0, and 2 are used. All other polynomials of the common radial order will not be used in the subsequent determination of the eyeglass prescription.

Alternatively, a method according in FIG. 4 could be conducted as follows. The method is for determining an eyeglass prescription of an eye. In a first step 310, a measurement indicative of the refractive properties of the eye is obtained. The measurement may be received as a data set or actually conducted. Again, this may be done via an aberrometer or other objective wavefront refraction as for example outlined together with FIG. 1 for step 110. In particular, information about a measurement indicative of the refractive properties of the eye is received by a processing unit.

Then, in step 320, a mathematical representation of wavefront aberrations of the eye from the measurement is determined, wherein the mathematical representation comprises a multitude of linearly independent functions, each function having an azimuthal order and a radial order, wherein the mathematical representation comprises at least a first group of functions having a common radial order, wherein the common radial order is higher than two.

Then, in step 330, the eyeglass prescription is determined based on a merit function, wherein the merit function comprises at least one function of the mathematical representation, and wherein each function of the first group of functions that is used in the merit function has an azimuthal order of −2, 0, or 2, wherein the merit function has a non-linear dependency on coefficients of the multitude of linearly independent functions.

Via the exemplary embodiments shown through FIGS. 2 to 4, an eyeglass prescription can be found via objective refraction techniques that is closer to the results found via subjective refraction techniques than if all Zernike polynomials up to a certain radial were used.

For estimation on how close a determination comes to a subjective refraction, an isolated analysis of the astigmatism has been conducted. The astigmatism difference was chosen because, unlike the mean power, it is relatively insensitive to any proximal accommodation. A set of 1000 eyes has been analyzed with similar people diameters ranging from 5.44 to 5.5 mm. Therefore, further pupil diameter dependent effects could be ignored.

Figure 5:
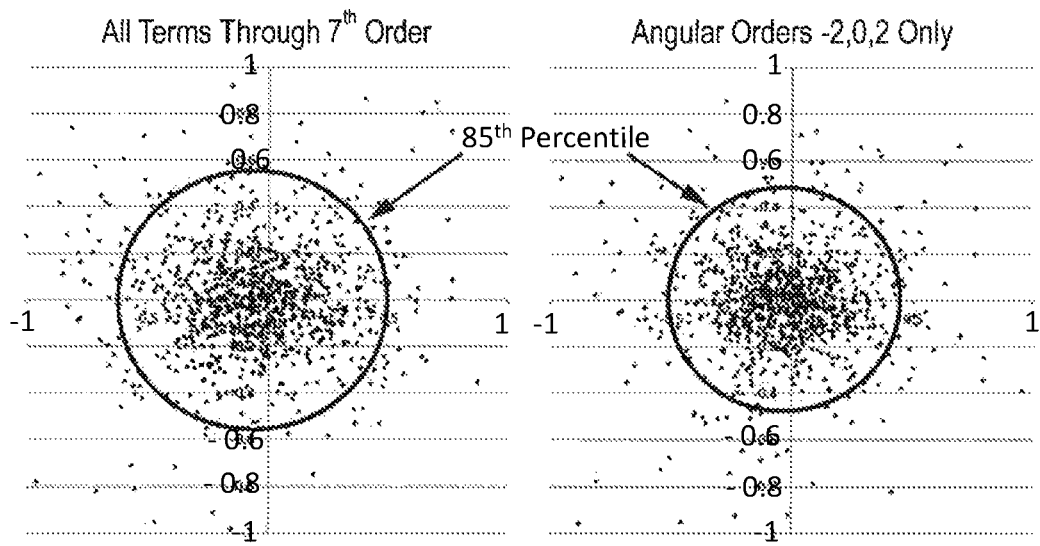
FIG. 5 shows example results and a closeness of the objective refraction results to the subjective refraction results.

To measure the "closeness" a vector difference between the calculated and the subjective cylindrical power was determined. The plots in FIG. 5 show the differences of the 1000 eyes for an example objective refraction and prescription calculation using Zernike polynomials through seventh order. This is shown on the left. Using the same calculation but only a subset of nine Zernike terms with angular order −2, 0, and 2 is shown on the right. Applying an 85% boundary, it was found that 85% of the eyes fall within a 0.555 diopters circle for the complete set of Zernike polynomials on the left. However, 85% of the glasses fall within a circle of 0.481 diopters using the restricted subset.

Figure 6:
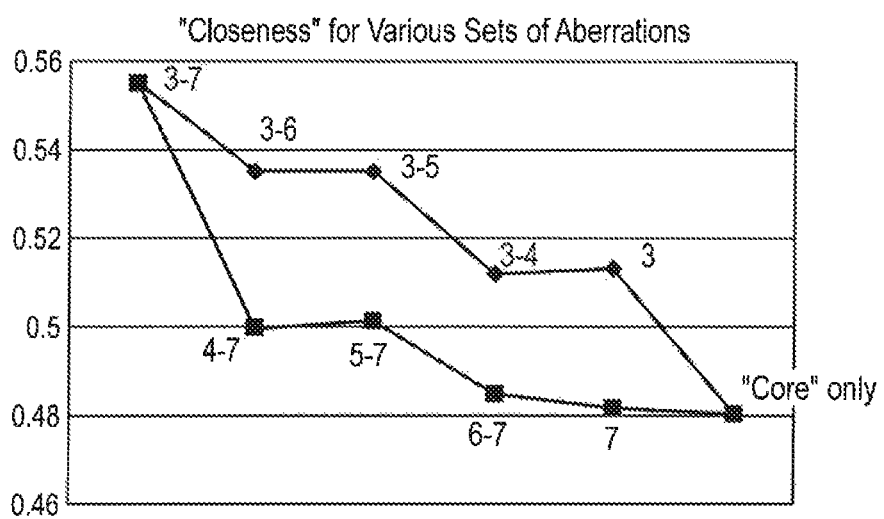
FIG. 6 shows example results for a closeness for different sets of Zernike polynomials.

Further, in FIG. 6, it was determined whether, within the set of Zernike polynomials, a reduction to only those of angular order −2, 0, and 2 would provide for the best closeness to the subjective refraction. The numbers next to the points in FIG. 6 show which radial order polynomials were included in the calculation in addition to the nine Zernike polynomials having an angular order of −2, 0, or 2 within the Zernike polynomials from second through seventh radial order. For example, the "3" point had only the nine "core" terms of angular orders −2, 0, and 2 plus the complete set of third order polynomials. For example the "3-5" included radial orders three through five completely, did not use any polynomial of the seventh radial order and, within the sixth radial order only the three Zernike polynomials having angular orders of −2, 0, and 2 were used. By this, various sets of Zernike polynomials were tested. All sets included the core terms which were nine terms in Zernike radial orders to through seven. Starting with the full set designated by "3-7" using the three second order terms and the full set of Zernike polynomials from third through seventh order, the set of Zernike polynomials was continuously restricted. The "4-7" point eliminated the four third radial order Zernike terms to only the remaining 29 Zernike polynomials were used, while "3-6" eliminated all eight seventh order terms leaving a 25 Zernike polynomials. The "3-5" contains fifteen terms with radial orders 3 through 5 plus three second order terms and three sixth order terms having an angular order of −2, 0, and 2 for a total of 27 Zernike terms. The results are quite obvious. The more the Zernike polynomials used were restricted, the better was the result, with a restricted set of Zernike polynomials using only the "core" of angular orders −2, 0, and 2 through the radial orders 2 to 7 performing best. "Best" here means that it resulted in an eyeglass prescription closest to the eyeglass prescription found via subjective refraction.

Figure 7:
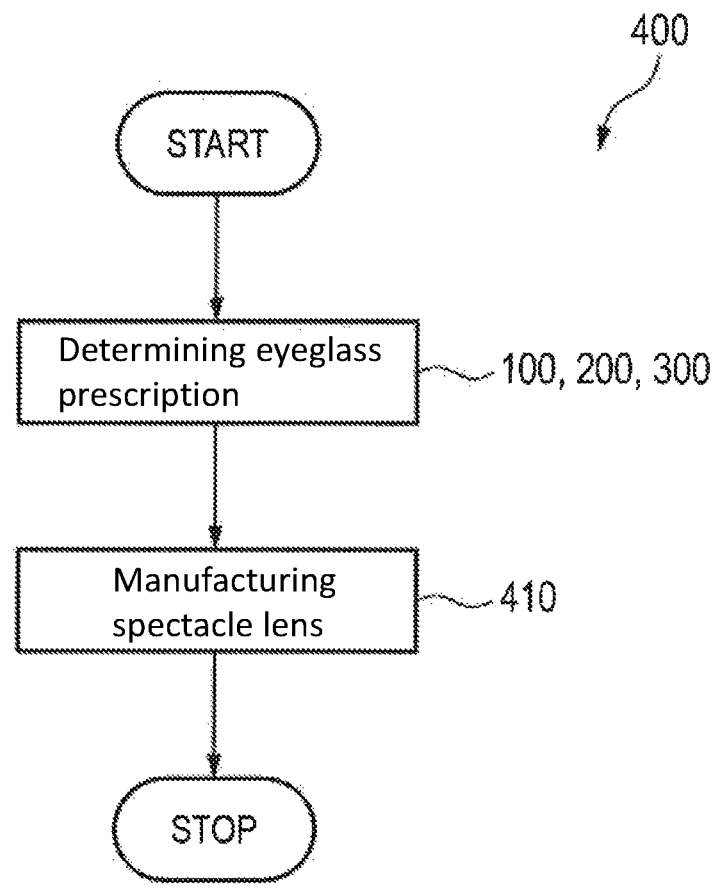
FIG. 7 shows an exemplary embodiment of a method for manufacturing a spectacle lens.

FIG. 7 shows a method for manufacturing a spectacle lens generally designated by, reference numeral 400. The eyeglass prescription for the spectacle lens can be determined via any of suggested methods 100, 200, and 300.

After the eyeglass prescription is determined, in step 410, the spectacle lens is manufactured according to the eyeglass prescription and to provide for the corresponding optical powers.

Figure 8:
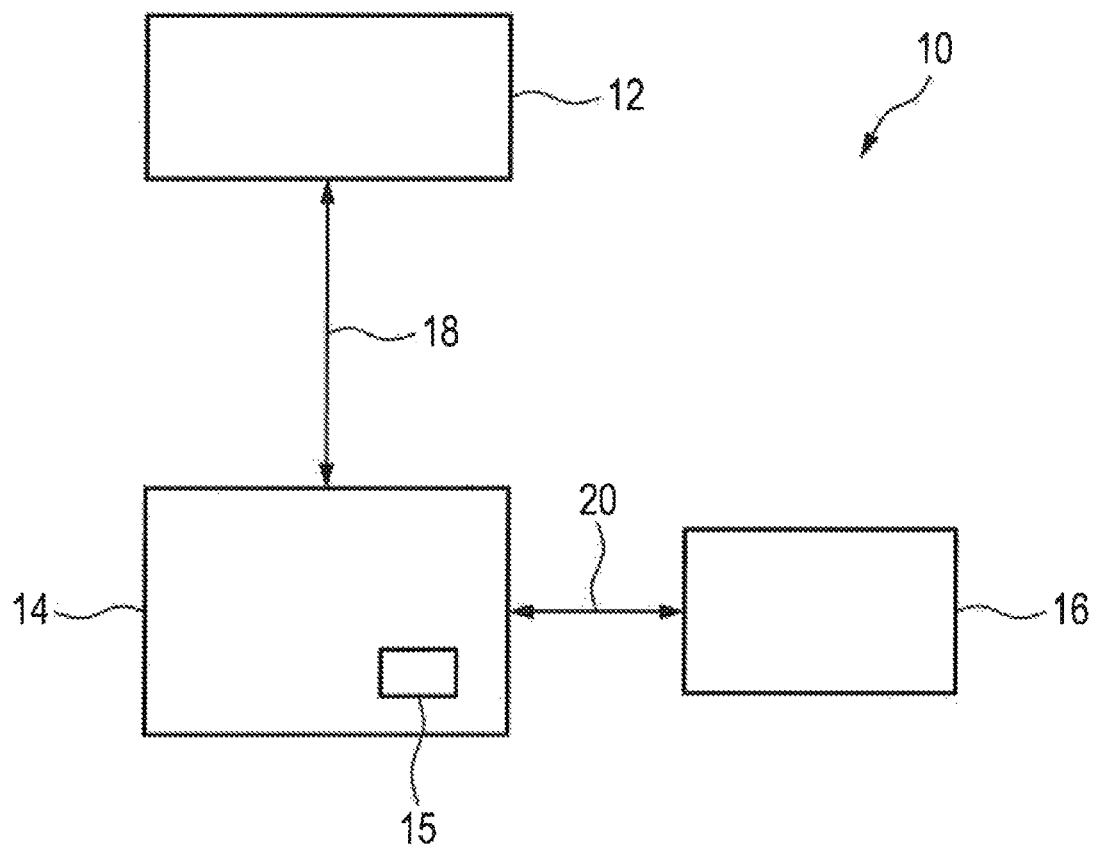
FIG. 8 shows an exemplary embodiment of a system.

FIG. 8 shows an exemplary embodiment of the system 10 according to the current disclosure. The optical wavefront aberration of a patient's eye can be determined via an aberrometer 12. Further, a subjective refraction may also be determinable. The calculation of the eyeglass prescription is then conducted on the processing unit 14. The processing unit 14 may comprise a computer program product 15 that stores executable program code to execute the methods explained above. Then, the system 10 may further comprise an output device 16 that may be a display, a printer or a storing device to output the determined eyeglass prescription to the output device 16. The aberrometer 12 is connected to the processing unit 14 via a line 18. The processing unit 14 is connected to the output device 16 via a line 20. Both lines 18 and 20 may each be a wired connection or a wireless connection for data transfer between the processing unit 14 from and to the aberrometer 12 and the output device 16.

The processing unit 14 may be configured to receive information about a measurement indicative of the refractive properties of the eye, to determine a mathematical representation of the refractive properties of the eye, wherein the mathematical representation comprises a multitude of polynomials, each polynomial having an azimuthal order and a radial order, wherein the mathematical representation comprises at least a first polynomial group 40, 42, 44, 46 having a common radial order, wherein the common radial order is higher than two, and to determine the eyeglass prescription based on a merit function, wherein the merit function comprises at least one polynomial of the mathematical representation, and wherein each polynomial of the first polynomial group 40, 42, 44, 46 and used in the merit function has an azimuthal order of −2, 0, or 2. Alternatively or additionally, the processing unit 14 may be configured to receive information about a measurement indicative of the refractive properties of the eye, to determine a mathematical representation of wavefront aberrations of the eye from the measurement, wherein the mathematical representation comprises a multitude of terms, wherein each term comprises a function dependent on the pupil radius, and wherein each term of the mathematical representation is either independent of an azimuthal angle or has a dependency on an azimuthal angle expressed by at least one of $\sin(2\Theta)$ and $\cos(2\Theta)$ with $\Theta$ being the azimuthal angle, and to determine the eyeglass prescription based on a merit function, wherein the merit function comprises at least one term of the mathematical representation. Alternatively or additionally, the processing unit 14 may be configured to receive information about a measurement indicative of the refractive properties of the eye, to determine a mathematical representation of wavefront aberrations of the eye from the measurement, wherein the mathematical representation comprises a multitude of polynomials, each polynomial having an azimuthal order and a radial order, wherein the mathematical representation comprises a polynomial group (40, 42, 44, 46) having a common radial order, wherein the common radial order is even and higher than two, and to determine the eyeglass prescription based on a merit function, wherein the merit function comprises at least one polynomial of the mathematical representation, and wherein the merit function only comprises the polynomials of the polynomial group (40, 42, 44, 46) having an azimuthal order of −2, 0, and 2, respectively.

By this, the system 10 is able to automatically determine an eyeglass prescription based on data provided via an aberrometer. However, instead of an aberrometer 12, the data underlying the optimization process may be also be acquired via the line 18 from a storing device that stores a multitude of patients' data acquired previously.

Figure 9:
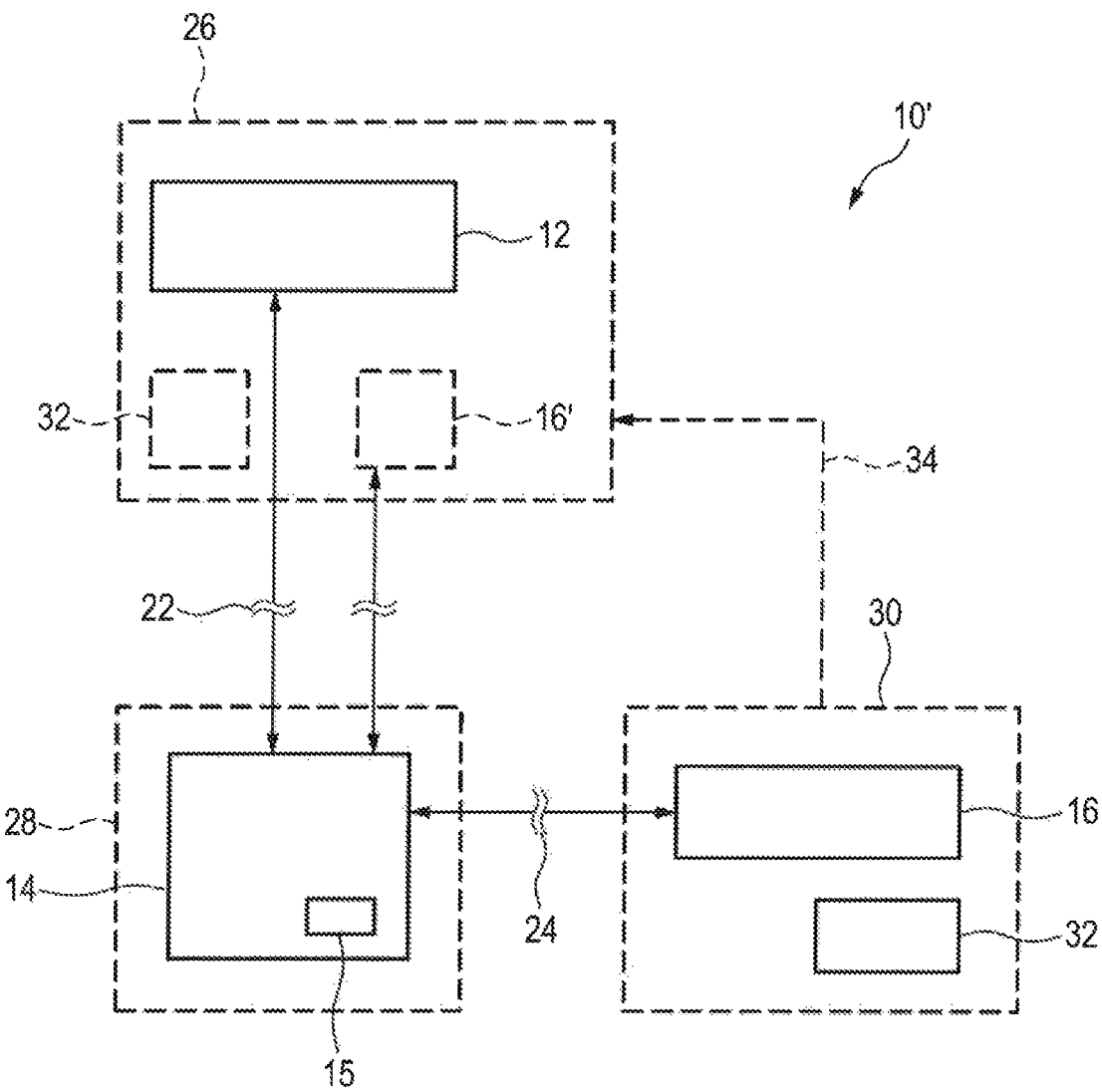
FIG. 9 shows a further exemplary embodiment of a system.

In FIG. 9, a further exemplary embodiment of the system 10' is shown. The aberrometer 12 may be located at a first site 26. The processing unit 14 is located at a second site 28. The output device 16 may be located at a third site 30 or may be also located at the first site 26. Further, a manufacturing unit 32 for manufacturing a spectacle lens may be present at either the third site 30 or the first site 26.

The first site 26, the second site 28 and the third site 30 are remote from each other. The first site 26 is connected with the second site 28 via a data network 22. The second site 28 and the third site 30 are connected via a data network 24. By this, it may be possible that refraction data provided via the aberrometer 12 can be sent to the processing unit 14. Further, a subjective refraction, in particular a subjective corrective astigmatism, may also be sent to the processing unit 14, for example from the first site 26 or any other site. Further, for example, the determined eyeglass prescription may then be sent back to the first site, for example a spectacle shop, to be recognized by an ophthalmologist and provided to, for example, the possible wearer. Further, the eyeglass prescription determined can also be forwarded to a remote manufacturing unit to manufacture the respective visual aid. The manufacturing unit can either be located at the first site 26. In this case, the data of the aberrometer is transmitted via connection 22 to the processing unit 14 at the second site 28 and then, the calculated eyeglass prescription is transferred back to the first site 26 and its possible manufacturing unit 32. Alternatively, from the second site 28, the determined eyeglass prescription can be transferred to a third site 30 with a possible manufacturing unit 32 to manufacture the visual aid. Last, it is possible that from this third site 30, the manufactured visual aid is then shipped to the first site 26 as indicated by the arrow 34.

Further, the disclosure comprises exemplary embodiments according to the following clauses:

Clause 1. A computer-implemented method (100, 200, 300) for determining an eyeglass prescription for an eye, the method comprising the steps of:

receiving (110, 210, 310) information about a measurement indicative of the refractive properties of the eye; and determining (120, 220, 320) a mathematical representation of wavefront aberrations of the eye from the measurement, wherein the mathematical representation comprises a multitude of polynomials, each polynomial having an azimuthal order and a radial order, wherein the mathematical representation comprises at least a first polynomial group (40, 42, 44, 46) having a common radial order, wherein the common radial order is higher than two;

wherein the method further comprises:

determining (130, 230, 330) the eyeglass prescription based on a merit function, wherein the merit function comprises at least one polynomial of the mathematical representation, and wherein each polynomial of the first polynomial group (40, 42, 44, 46) that is used in the merit function has an azimuthal order of −2, 0, or 2.

Clause 2. The method of clause 1, characterized in that, from polynomials of the mathematical representation having a radial order below three, the merit function is only based on polynomials having the second radial order.

Clause 3. The method of clause 1 or 2, the method being characterized by:

establishing an optimization space corresponding to a plurality of possible eyeglass prescriptions for the eye: and wherein the eyeglass prescription is determined by optimizing a value of the merit function, wherein the value of the merit function corresponds to a visual function of the eye when corrected using one of the plurality of possible eyeglass prescriptions within the optimization space.

Clause 4. The method of any of clauses 1 to 3, characterized in that the common radial order of the first polynomial group (40, 42, 44, 46) is even, and wherein the merit function only comprises three polynomials having an azimuthal order of −2, 0, and 2, respectively, of the first polynomial group (40, 42, 44, 46).

Clause 5. The method of any of clauses 1 to 4, characterized in that only a reduced number of polynomials having the common radial order is used in the merit function compared to a number of polynomials within the first polynomial group (40, 42, 44, 46) of the mathematical representation, and wherein the reduced polynomial group used in the merit function only comprises polynomials having an azimuthal order of −2, 0, or 2.

Clause 6. The method of any of clauses 1 to 4, characterized in that the first polynomial group (42, 46) in the mathematical representation comprises polynomials each having an azimuthal order different from −2, 0, and 2, and wherein no polynomial of the first polynomial group (42, 46) is used in the merit function.

Clause 7. The method of any of clauses 1 to 8, characterized in that the mathematical representation is determined using Zernike polynomials.

Clause 8. The method of clause 7, characterized in that the mathematical representation includes Zernike polynomials up to and including seventh radial order, wherein the merit function is based only on Zernike polynomials of the second radial order and. Zernike polynomials having a radial order higher than two.

Clause 9. The method of clause 8, characterized in that the common radial order of the first polynomial group (40, 42, 44, 46) is the third order, the fourth order, the fifth order, the sixth order, or the seventh order.

Clause 10. The method of any of clauses 7 to 9, characterized In that, in case the common radial order of the first polynomial group (44) is even, the merit function only comprises the polynomials of azimuthal orders of −2, 0, and 2, respectively, and in that, in case the common radial order of the first polynomial group (40, 42) is odd, the merit function comprises no polynomial of the first polynomial group (40, 42, 48).

Clause 11. The method of any of clauses 7 to 10, characterized in that the mathematical representation comprises at least a second polynomial group (40, 42, 44, 46) having a common radial order and different from the first polynomial group (40, 42, 44, 46), wherein the common radial order of the second polynomial group (40, 42, 44, 46) is higher than two, and wherein, in case the common radial order of the second polynomial group (40, 42, 44, 46) is even, the merit function only comprises the polynomials of azimuthal orders of −2, 0, and 2, respectively, and, in case the common radial order of the second polynomial group (40, 42, 44, 46) is odd, the merit function comprises no polynomial of the second polynomial group (40, 42, 44, 46).

Clause 12. The method of any of clauses 7 to 11, characterized in that the merit function is only based on the Zernike polynomials having an azimuthal order of −2, 0, and 2, respectively.

Clause 13. The method of any of clauses 7 to 10, characterized in that the mathematical representation comprises at least a second polynomial group (40, 42, 44, 46) having a common radial order and different from the first polynomial group (40, 42, 44, 46), wherein the common radial order of the second polynomial group (40, 42, 44, 46) is higher than two, and wherein, of each polynomial group (40, 42, 44, 46) having an even radial order, the merit comprises ail Zernike polynomials, and wherein, of each polynomial group (40, 42, 44, 46) having an odd order, the merit function comprises no polynomial.

Clause 14. The method of any of clauses 1 to 4, characterized in that the mathematical representation is determined to comprise only polynomials having an azimuthal order of −2, 0, or 2.

Clause 15. The method of clause 14, characterized in that the mathematical representation is determined in the form of $$W = f_{-2}(r)\cos(2\cdot\Theta) + f_0(r) + f_2(r)\sin(2\cdot\Theta),$$

wherein $f_{-2}(r)$, $f_0(r)$, and $f_2(r)$ functions of the radius of a pupil of the eye, and wherein W is the wavefront aberration of the eye.

Clause 16. A computer-implemented method (200) for determining an eyeglass prescription for an eye, the method comprising the steps of:
receiving (210) information about a measurement indicative of the refractive properties of the eye;
wherein the method further comprises:

determining (220) a mathematical representation of wavefront aberrations of the eye from the measurement, wherein the mathematical representation comprises a multitude of terms, wherein each term comprises a function dependent on the pupil radius, and wherein each term of the mathematical representation is either independent of an azimuthal angle or has a dependency on an azimuthal angle expressed by at least one of sin(29) and cos(20) with 6 being the azimuthal angle; and
determining (230) the eyeglass prescription based on a merit function, and wherein the merit function comprises at least one term of the mathematical representation.

Clause 17. The method according to clause 18, wherein the function dependent on the pupil radius of each term is a polynomial, wherein each polynomial has a radial order, and wherein the highest radial order is higher than two.

Clause 18. The method according to clause 16, wherein the function dependent on the pupil radius of each term is a Fourier series or wherein the function dependent on the pupil radius of each term is a spline function.

Clause 19. A computer-implemented method (300) for determining an eyeglass prescription for an eye, the method comprising the steps of:
receiving (310) information about a measurement indicative of the refractive properties of the eye; and
determining (320) a mathematical representation of wavefront aberrations of the eye from the measurement, wherein the mathematical representation comprises a multitude of polynomials, each polynomial having an azimuthal order and a radial order, wherein the mathematical representation comprises a polynomial group (40, 42, 44, 46) having a common radial order, wherein the common radial order is even and higher than two;
wherein the method further comprises:
determining (330) the eyeglass prescription based on a merit function, wherein the merit function comprises at least one polynomial of the mathematical representation, and wherein the merit function only comprises the polynomials of the polynomial group (40, 42, 44, 46) having an azimuthal order of −2, 0 and 2, respectively.

Clause 20. A method (400) for manufacturing a spectacle lens, the method comprising the steps of:
determining (100, 200, 300) an eyeglass prescription according to a method of any of clauses 1 to 15; and
manufacturing (410) the spectacle lens according to the eyeglass prescription.

Clause 21. A method (400) for manufacturing a spectacle lens, the method comprising the steps of:
determining (100, 200, 300) an eyeglass prescription according to a method of any of clauses 18 to 18; and
manufacturing (410) the spectacle lens according to the eyeglass prescription.

Clause 22. A method (400) for manufacturing a spectacle lens, the method comprising the steps of:
determining (100, 200, 300) an eyeglass prescription according to a method of clause 19; and
manufacturing (410) the spectacle lens according to the eyeglass prescription.

Clause 23. A system (10) for determining an eyeglass prescription for an eye, comprising a processing unit (14) configured to receive information about a measurement indicative of the refractive properties of the eye, to determine a mathematical representation of the refractive properties of the eye, wherein the mathematical representation comprises a multitude of polynomials, each polynomial having an azimuthal order and a radial order, wherein the mathematical representation comprises at least a first polynomial group (40, 42, 44, 46) having a common radial order, wherein the common radial order is higher than two, and to determine the eyeglass prescription based on a merit function, wherein the merit function comprises at least one polynomial of the mathematical representation, and wherein each polynomial of the first polynomial group (40, 42, 44, 46) and used in the merit function has an azimuthal order of −2, 0, or 2.

Clause 24. The system of clause 23, further comprising a measurement device (12) for measuring the refractive properties of the eye, wherein the measurement device (12) is located at a first site (28), wherein the processing unit (14) is located at a second site (28), and wherein the first site (26) and the second site (28) are connected via a data network (22).

Clause 25. A system (10) for determining an eyeglass prescription for an eye, comprising a processing unit (14) configured to receive information about a measurement indicative of the refractive properties of the eye, to determine a mathematical representation of wavefront aberrations of the eye from the measurement, wherein the mathematical representation comprises a multitude of terms, wherein each term comprises a function dependent on the pupil radius, and wherein each term of the mathematical representation is either independent of an azimuthal angle or has a dependency on an azimuthal angle expressed by at least one of $\sin(2\Theta)$ and $\cos(2\Theta)$ with $\Theta$ being the azimuthal angle, and to determine the eyeglass prescription based on a merit function, wherein the merit function comprises at least one term of the mathematical representation.

Clause 26. The system of clause 25, further comprising a measurement device (12) for measuring the refractive properties of the eye, wherein the measurement device (12) is located at a first site (26), wherein the processing unit (14) is located at a second site (28), and wherein the first site (26) and the second site (28) are connected via a data network (22).

Clause 27. A system (10) for determining an eyeglass prescription for an eye, comprising a processing unit (14) configured to receive information about a measurement indicative of the refractive properties of the eye, to determine a mathematical representation of wavefront aberrations of the eye from the measurement, wherein the mathematical representation comprises a multitude of polynomials, each polynomial having an azimuthal order and a radial order, wherein the mathematical representation comprises a polynomial group (40, 42, 44, 46) having a common radial order, wherein the common radial order is even and higher than two, and to determine the eyeglass prescription based on a merit function, wherein the merit function comprises at least one polynomial of the mathematical representation, and wherein the merit function only comprises the polynomials of the polynomial group (40, 42, 44, 46) having an azimuthal order of −2, 0, and 2, respectively.

Clause 28. The system of clause 27, further comprising a measurement device (12) for measuring the refractive properties of the eye, wherein the measurement device (12) is located at a first site (26), wherein the processing unit (14) is located at a second site (28), and wherein the first site (26) and the second site (28) are connected via a data network (22).

Clause 29. A, in particular non-transitory, computer program product (15) comprising program code means for carrying out the steps of a method (100, 200, 300) according to any of clauses 1 to 15, in particular when the computer program product is run on a computer or processing unit (12).

Clause 30. A, in particular non-transitory, computer program product (15) comprising program code means for carrying out the steps of a method (100, 200, 300) according to any of clauses 16 to 18, in particular when the computer program product is run on a computer or processing unit (12).

Clause 31 A, in particular non-transitory, computer program product (15) comprising program code means for carrying out the steps of a method (100, 200, 300) according to clause 19, in particular when the computer program product is run on a computer or processing unit (12).

The foregoing description of the exemplary embodiments of the disclosure illustrates and describes the present disclosure. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A computer-implemented method for determining an eyeglass prescription for an eye, the method comprising:
receiving information about a measurement indicative of refractive properties of the eye;
determining a mathematical representation of wavefront aberrations of the eye from the measurement,
wherein the mathematical representation includes a multitude of terms, wherein each term from among the multitude of terms includes a function dependent on a pupil radius, and wherein each term of the mathematical representation is either independent of an azimuthal angle or has a dependency on an azimuthal angle expressed by at least one of $\sin(2\theta)$ and $\cos(2\theta)$ with $\theta$ being an azimuthal angle; and
determining the eyeglass prescription based on a merit function, wherein the merit function includes at least one term of the mathematical representation.

2. A computer-implemented method for determining an eyeglass prescription for an eye, the method comprising:
receiving information about a measurement indicative of refractive properties of the eye;
determining a mathematical representation of wavefront aberrations of the eye from the measurement,
wherein the mathematical representation includes a multitude of terms, wherein each term from among the multitude of terms includes a function dependent on a pupil radius, and wherein each term of the mathematical representation is either independent of an azimuthal angle or has a dependency on an azimuthal angle expressed by at least one of $\sin(2\theta)$ and $\cos(2\theta)$ with $\theta$ being an azimuthal angle; and determining the eyeglass prescription based on a merit function, wherein the merit function includes at least one term of the mathematical representation, wherein the function dependent on the pupil radius of each term is a polynomial, wherein each polynomial has a radial order, and wherein a highest radial order is higher than two.

3. The method according to claim 1, wherein the function dependent on the pupil radius of each term is a Fourier series or wherein the function dependent on the pupil radius of each term is a spline function.

4. A method for manufacturing a spectacle lens, the method comprising:
   determining an eyeglass prescription according to the method of claim 1; and
   manufacturing the spectacle lens according to the eyeglass prescription.

5. A system for determining an eyeglass prescription for an eye, the system comprising:
   a processing unit configured to:
      receive information about a measurement indicative of the refractive properties of the eye;
      determine a mathematical representation of wavefront aberrations of the eye from the measurement, wherein the mathematical representation includes a multitude of terms, wherein each term from among the multitude of terms includes a function dependent on a pupil radius, and wherein each term of the mathematical representation is either independent of an azimuthal angle or has a dependency on an azimuthal angle expressed by at least one of $\sin(2\theta)$ and $\cos(2\theta)$ with $\theta$ being the azimuthal angle; and
      determine the eyeglass prescription based on a merit function, wherein the merit function comprises at least one term of the mathematical representation.

6. The system of claim 5, further comprising:
   a measurement device for measuring the refractive properties of the eye, wherein the measurement device is located at a first site, wherein the processing unit is located at a second site, and wherein the first site and the second site are connected via a data network.

7. A computer program product stored on a non-transitory storage medium and having program code means for carrying out the method according to claim 1.

* * * * *